United States Patent
Berke et al.

(10) Patent No.: US 6,871,654 B1
(45) Date of Patent: Mar. 29, 2005

(54) FRUIT AND VEGETABLE SONIC WASHER AND METHOD

(75) Inventors: Joseph J. Berke, West Bloomfield, MI (US); Charles T. Michael, Troy, MI (US)

(73) Assignee: Berke-Tec, Inc.,, Detroit, MI (US)

( * ) Notice: Subject to any disclaimer, the term of this patent is extended or adjusted under 35 U.S.C. 154(b) by 309 days.

(21) Appl. No.: 10/162,493

(22) Filed: Jun. 5, 2002

(51) Int. Cl.[7] .............................. B08B 7/04; B08B 3/02; B08B 7/02
(52) U.S. Cl. .......................... 134/25.3; 134/1; 134/111; 134/184; 134/186
(58) Field of Search .......................... 134/25.3, 1, 186, 134/184, 111; 422/20, 127, 128, 300

(56) References Cited

U.S. PATENT DOCUMENTS

| | | | |
|---|---|---|---|
| 4,236,541 A | 12/1980 | Cipriani | |
| 5,113,881 A | 5/1992 | Lin et al. | |
| 5,437,731 A | * 8/1995 | St. Martin | .................... 134/10 |
| 5,660,195 A | * 8/1997 | Taylor et al. | ............. 134/58 D |
| 5,858,116 A | * 1/1999 | Kim | .......................... 134/25.3 |
| 5,927,304 A | * 7/1999 | Wen | ............................ 134/153 |
| 6,033,705 A | 3/2000 | Isaacs | |
| 6,117,468 A | 9/2000 | Mumme | |
| 6,514,349 B1 | * 2/2003 | Meldrum | ....................... 134/1 |
| 6,640,818 B1 | * 11/2003 | Talisman | ..................... 134/89 |

* cited by examiner

Primary Examiner—Alexander Markoff
(74) Attorney, Agent, or Firm—Alex Rhodes

(57) ABSTRACT

A sonic fruit and vegetable washer for removing inorganic impurities and pathogens from a variety of raw fruit and vegetables. The sonic fruit and vegetable washer is comprised of a housing, a removable basket, a liquid dispenser, a filter, a sonic generator, a spray head, hydraulic values, electrical controls, a blower, and a heating element. The washer is connected to an existing faucet, and drains into a conventional kitchen sink. During a typical operation, the controls are adjusted for a particular fruit or vegetable, a fruit or vegetable is loaded into the basket, and a small amount of a preservative, cleaning agent, sweetener or vitamin or mineral is added and electrical power is applied. Water enters the washer, is filtered, and one or more wash and rinse cycles are completed. The sonic generator is active during the wash and rinse cycles to remove and flush contaminants from the washer. Thereafter, a drying cycle is completed.

27 Claims, 7 Drawing Sheets

FRUIT AND VEGETABLE SONIC WASHER AND METHOD

FIELD OF THE INVENTION

This invention relates to washing and cleaning and more particularly to a sonic household appliance and method for cleaning and disinfecting fruits and vegetables.

BACKGROUND OF THE INVENTION

Contaminants and impurities, such as dirt, fertilizers, fungicides, feces, molds, insects, bacteria and microbial pathogens can be the cause of disagreeable taste in raw fruits and vegetables and often cause indigestion, diarrhea, gastroenteritis, chronic and acute illness and sometimes fatalities. Microbial pathogens may also occur in either municipal and well water (e.g. parasites, viruses and bacteria) from sewage treatment plants, septic systems or agricultural livestock operations. Also, inorganic impurities, such as salts and metals, naturally occurring or derived from urban storm water runoff, industrial wastewater discharges, oil and gas production, mining and farming are distasteful as well.

The present practice is to remove contaminants by soaking, rinsing and/or scrubbing raw fruits and vegetables with municipal or well water. This practice is unsatisfactory for complete cleaning and does not remove all of the impurities in municipal and well water. Additional contaminants may exist beneath the wax coatings of fruits and vegetables, such as, apples, cucumbers, carrots and onions. Moreover, leafy vegetables (e.g. berries, grapes, plums and apricots) are easily damaged during scrubbing.

SUMMARY OF THE INVENTION

The present invention is an effective kitchen appliance and method for removing impurities from a wide variety of raw fruits and vegetables. Although primarily directed to households, the appliance is also applicable to commercial establishments, such as restaurants and banquet halls. One benefit of the invention is that it is effective for cleaning and disinfecting a wide variety of vegetables and fruits, including, but not limited to leafy vegetables, such as broccoli, lettuce and spinach, and delicate fruits, such as berries, plums, grapes and apricots. Still yet another benefit is that changes in an existing kitchen are unnecessary. Portability is still yet another benefit.

The fruit and vegetable washer is comprised of a housing, a removable basket, a liquid dispenser, a filter, a sonic generator, a spray head, a blower, a pair of valves, and controls and a heating element. The blower and heating element are optional to enhance the invention's cleaning effect. A preferred embodiment is adapted to be connected to an existing water source, such as a kitchen faucet, and drains into a conventional kitchen sink.

During a typical operation, the washer is connected to the kitchen faucet and an end of a drain hose is placed in a kitchen sink. The controls are adjustable for a particular fruit or vegetable. A fruit or vegetable is loaded into the basket and a small amount of a liquid, such as a preservative, bactericidal or bacteriostatic cleaning agent, sweetener or vitamin or mineral supplement is discharged from the dispenser into the basket which has been loaded with the fruit or vegetable. Electrical power is applied with an on/off switch causing water to enter the washer and pass through the filter into the basket. The sonic generator is activated followed by one or more wash and rinse cycles to remove and flush the contaminants from the washer. The final cycle is a drying cycle wherein the blower and heating element are active.

In employing the teaching of the present invention, a plurality of alternate constructions can be adopted to achieve the desired results and capabilities. In this disclosure, several embodiments are discussed. However, the disclosed embodiment is intended as an example only and should not be considered as limiting the scope of the invention.

Further features and benefits will be apparent by reference to the drawings and ensuing detailed description of a preferred embodiment which discloses the best mode contemplated in carrying out the invention. The exclusive rights which are claimed are set forth in the numbered claims following the detailed description of the preferred embodiment.

BRIEF DESCRIPTION OF THE DRAWINGS

The invention will be better understood and further objects, characterizing features, details and advantages thereof will appear more clearly with reference to the diagrammatic drawings illustrating a preferred embodiment of the invention by way of non-limiting example only.

DETAILED DESCRIPTION OF THE PREFERRED EMBODIMENT

Figure 1:
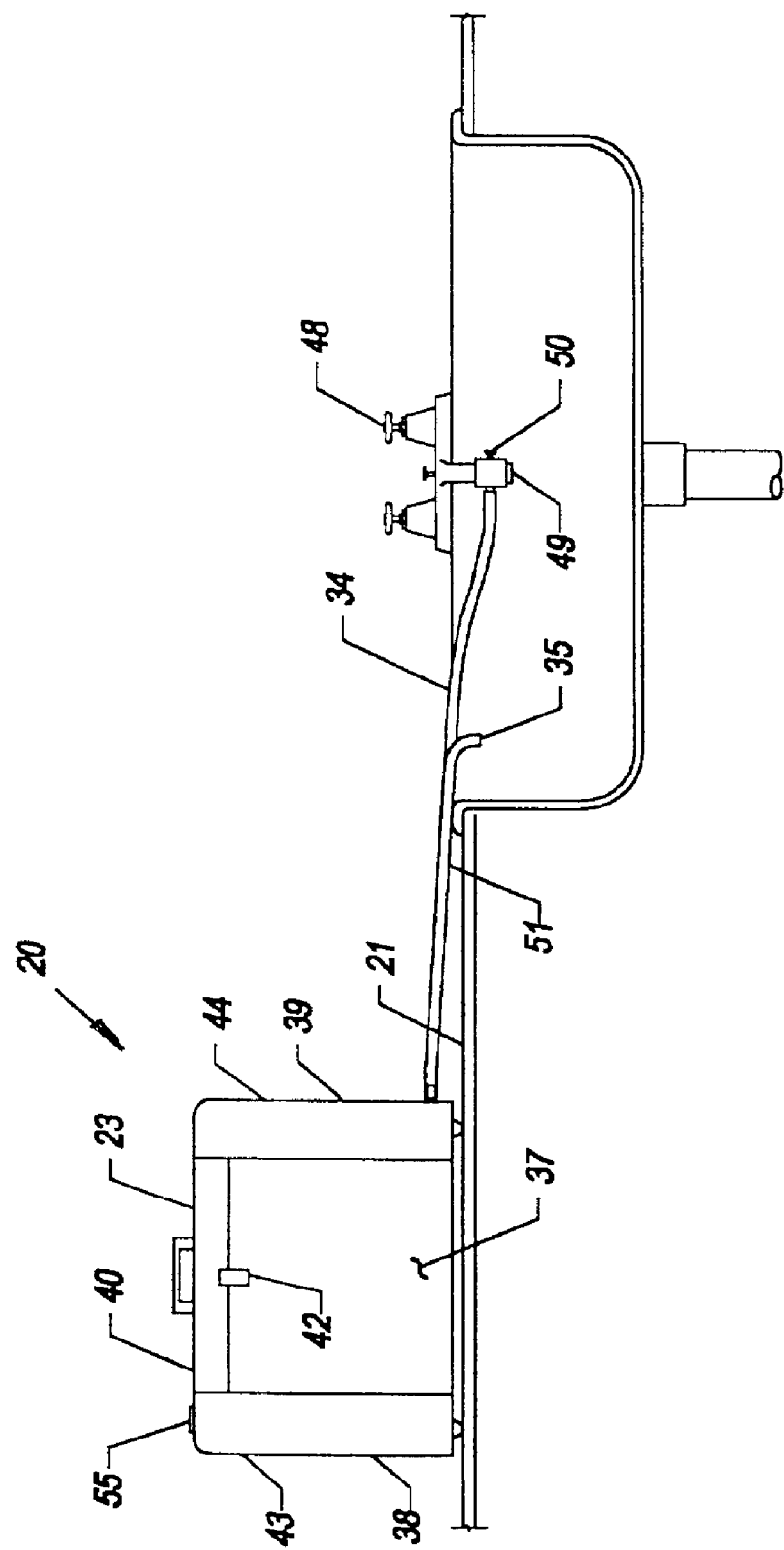
FIG. 1 is a front view of a fruit and vegetable washer on a counter-top according to the invention.

Referring now to the drawings in which like numerals designate similar and corresponding parts throughout the several views, in FIG. 1 a washer 20 for cleaning and disinfecting fruits and vegetables is shown on a typical counter-top 21 and sink 22. The washer 20 is intended for use in a private residence but is applicable to institutions such as hospitals, and businesses such as restaurants and banquet halls.

The washer 20 is comprised of a housing 23, a basket 24, a dispenser 25, a filter 26, a sonic generator 27, a spray head 28, an exhaust fan 29, a pair of solenoid water valves 30, 31, a control unit 32, a water level switch 33, a pair of hoses 34, 35 and a heating element 36. The housing 23 has three sections. One section is a tank 37 for holding and washing fruits and vegetables. A second section is a control section 38 for operating the washer 20. A third section is a valve and filter section 39 for filtering and controlling the flow of water. A top cover 40 is pivotally mounted to the tank 37 with a hinge 41 and is locked in a down position with a clasp 42. A pair of removable end covers 43, 44 are attached to opposite ends of the tank 37 for covering and servicing the control unit 32, the valves 30, 31 and the filter 26.

The exhaust fan 29 and dispenser 25 are located in the interior of the top cover 40. During a drying cycle, air is drawn into a tank 37 through a first group of slotted openings 46 in the top cover 40 by the fan 29 and is discharged through a second group of slotted openings 47 in the top cover 40. At one end of the tank 37 an inlet tube 34 is attached to a solenoid operated inlet valve 30 for adding water to the tank 37 and an outlet tube 35 is attached to a solenoid operated outlet valve 31 for draining water from the tank 37. The inlet tube 34, as shown in FIG. 1, is attached to a faucet 48 with a usual type of adapter 49. The adapter 49 includes a diverter valve 50 for diverting water into the tank 37 or into the sink 22. The outlet tube 35 has an elbow 51 which extends into the sink 22 for draining water into the sink 22.

Figure 2:
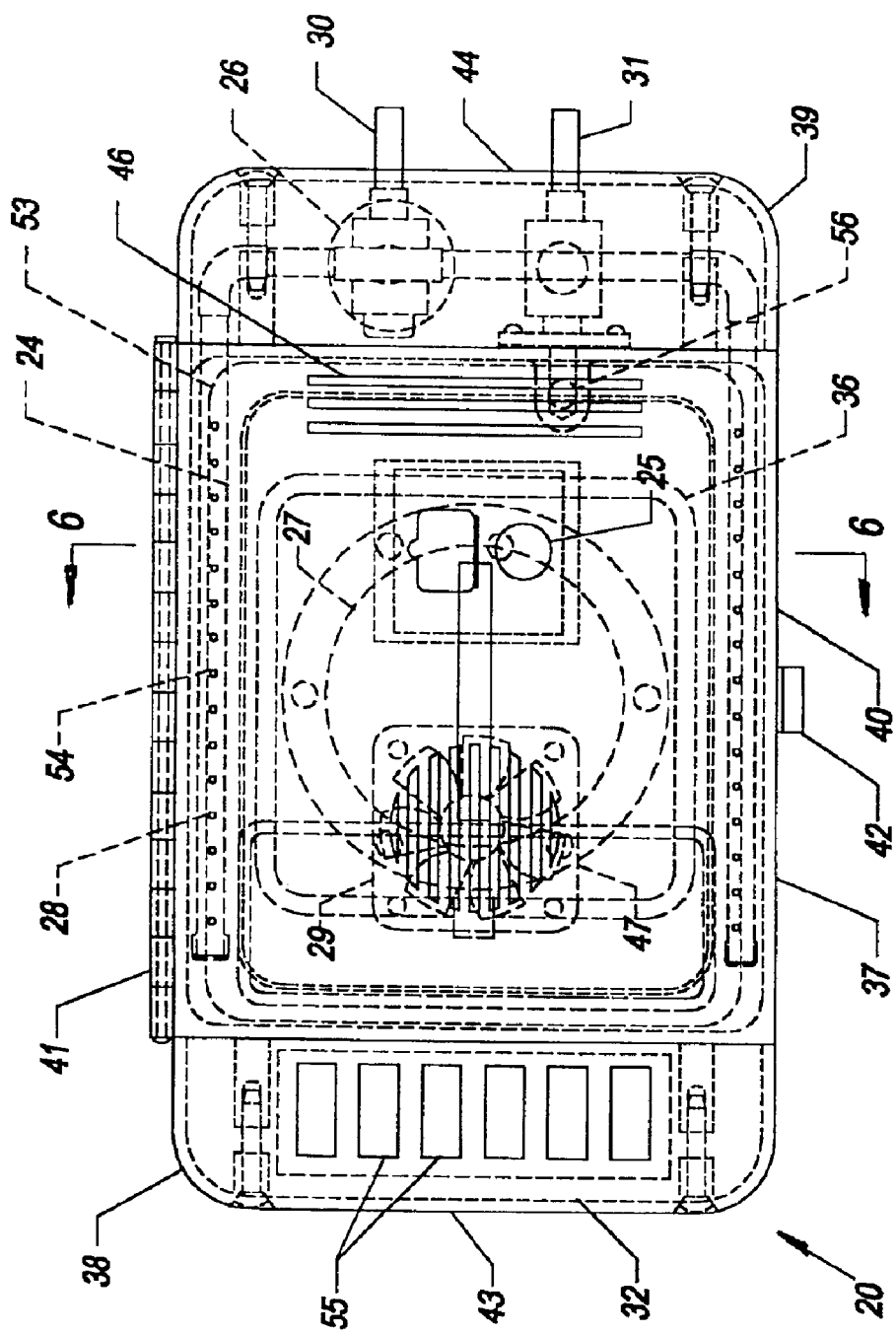
FIG. 2 is a plan view of the fruit and vegetable washer.
Figure 3:
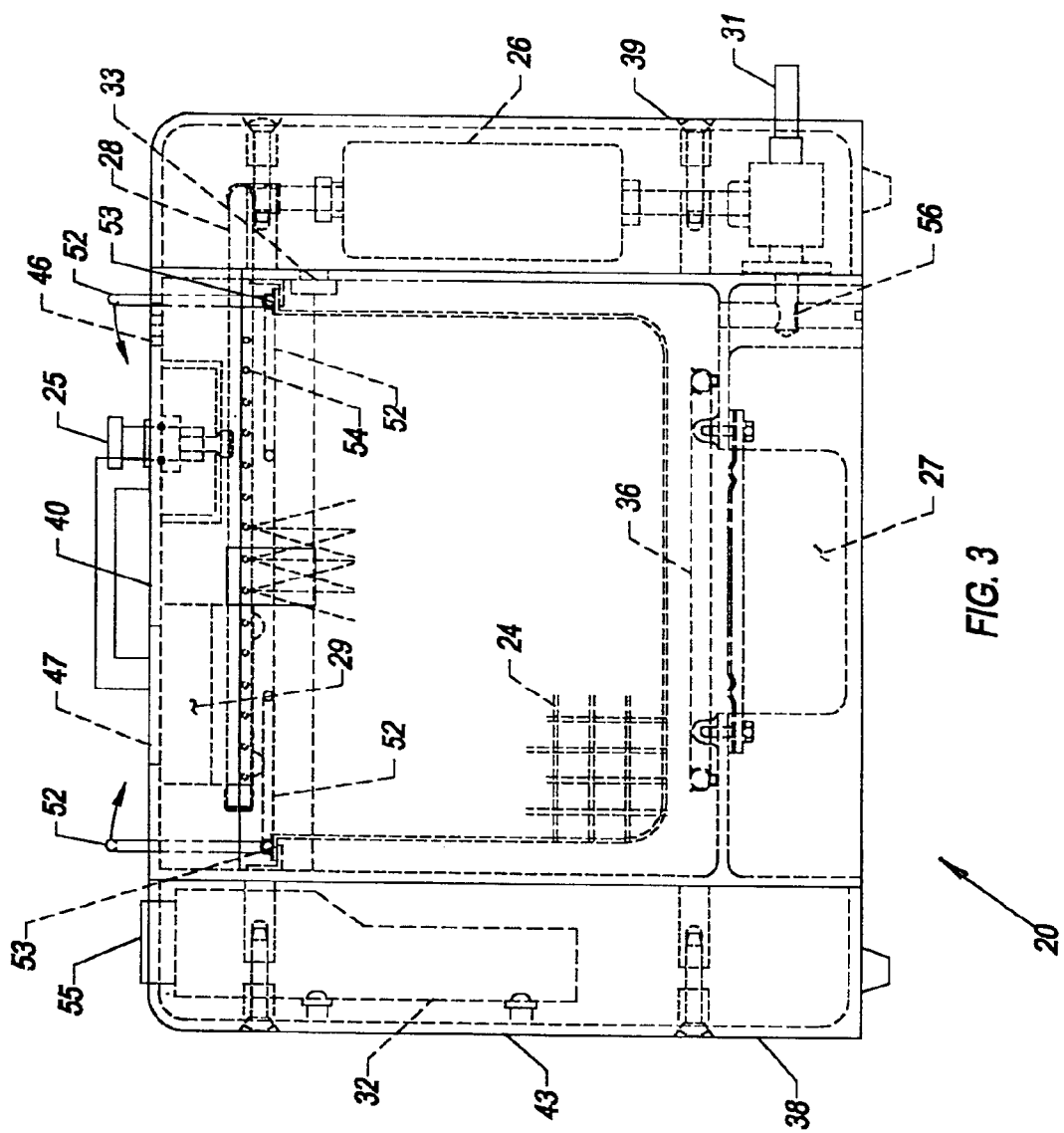
FIG. 3 is front view of the fruit and vegetable washer.
Figure 6:
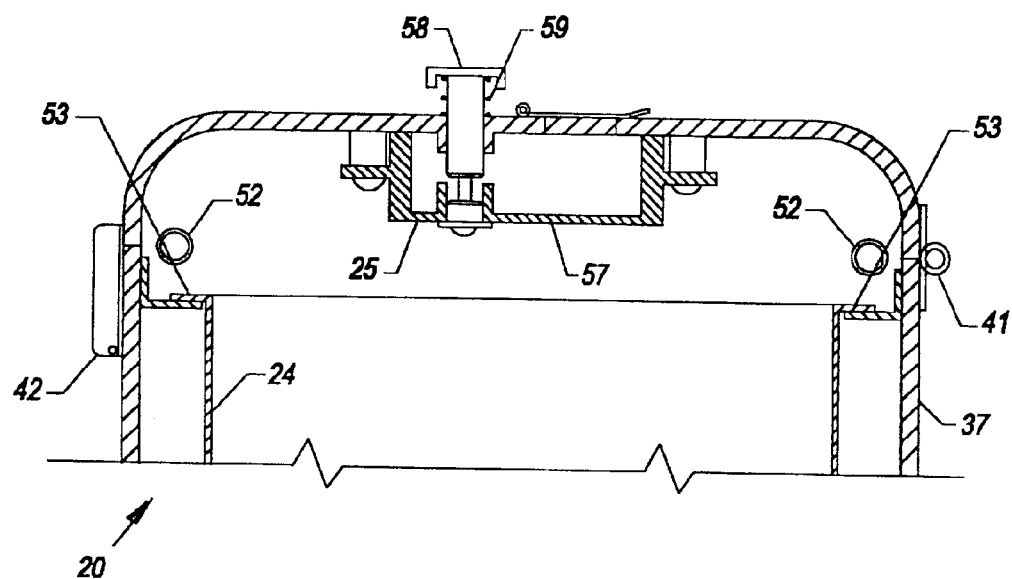
FIG. 6 is an enlarged cross-sectional view taken on the line 6—6 in FIG. 2 showing a dispensing valve in a closed position.

The relationships between the various parts of the invention are best understood by reference to FIGS. 2, 3 and 6. Within the tank 37 are the wire basket 24, the sonic generator 27, the spray head 28 and the heating element 36. The wire basket 24 is removable to facilitate loading and unloading fruits or vegetables and for cleaning the basket 24 and tank 37. A pair of wire handles 52 are pivotally attached to top portions of the wire basket 24 for ease in removing and installing the basket 24. In FIG. 3, the handles 52 are shown in vertical positions for basket removal. The wire basket 24 is supported in the tank by flanges 53 of the basket 24.

The spray head 28, positioned above the basket 24, is a U-shaped tube with perforations 54 along front and rear tubular portions of the spray head 28 for discharging water into the tank 37. The spray head 28 is connected to the filter 26. The tubular heating element 36 is used to promote drying and for enhancing the cleaning and disinfecting of fruits and vegetables.

The sonic generator 27, below the basket 24, is removably attached to a bottom wall of the tank 37. The sonic generator 27 may be a single or dual frequency generator. A preferred dual generator 27 for the cleaning and heavy scrubbing of fruits and vegetables consists of an audio frequency generator and a general purpose ultrasonic generator. The audio frequency portion provides the additional psychological benefit of allowing users to know that the washer 20 is operational. Ultrasonic frequency sonic generators having frequencies of 32 to 38 khz have been found to be effective for removing bacteria and microbial pathogens from fruits and vegetables (U.S. Pat. No. 5,113,881).

The control unit 45, removably attached to one of the end covers 43, includes a series of push buttons 55, a usual type power supply (not shown), and usual types of timing, multivibrator and amplifier circuits (not shown). The push buttons 55 include an "on/off" push button and push buttons for cleaning a variety of different and specific fruits and vegetables. The control unit 45 varies the frequency and amplitude of the sonic generator 27, the duty cycles of the sonic generator 27, valves 30, 31, fan 29, heating element 36 and the sequencing of events (i.e., cleaning, rinsing, heating, and drying).

When the washer 20 is operative, water from the sink faucet 48 passes through the inlet tube 34, the inlet valve 30, the filter 26, and spray head 28 and is discharged through the perforations 54 of the spray head 28 into the wire basket 24. Water is drained from the tank 37 through the outlet valve 31, the outlet tube 35 and into the sink 22. The outlet tube 35 is connected to the outlet valve 31 by a port 56 at the bottom of the tank 37. The outlet port is below the level of the water of the tank to insure that the tank 37 can be fully drained.

Figure 7:
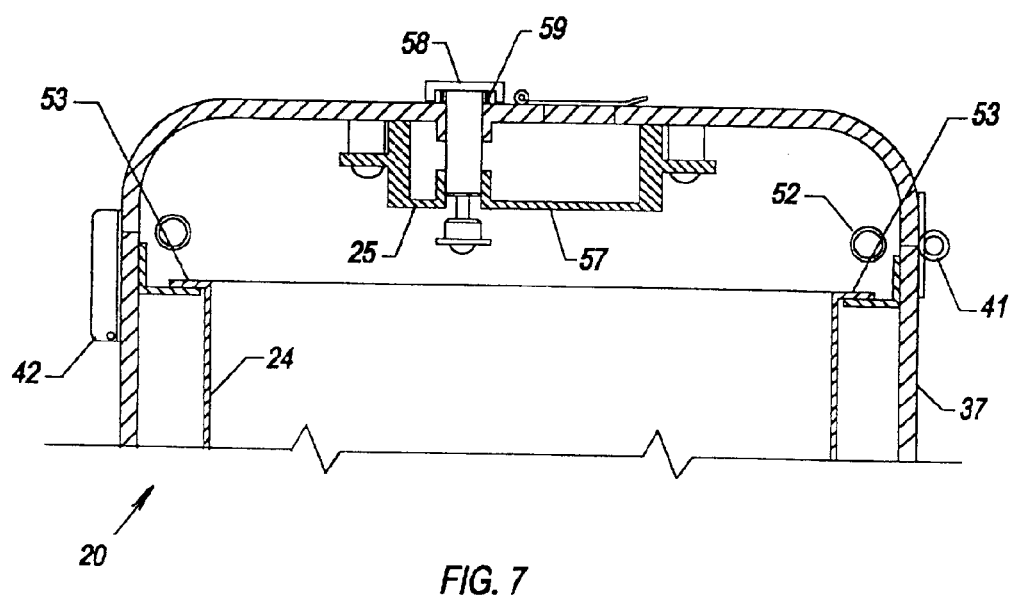
FIG. 7 is an enlarged cross-sectional view taken in the same manner as FIG. 6, showing the dispensing valve in an open position.

The dispenser 25 is illustrated in FIGS. 6 and 7 and is comprised of a housing 57, a spool 58 and a spring 59. The dispenser 25 is shown in a closed position in FIG. 6 and in an open position in FIG. 7. After an opening, the spool 58 is biased by the spring 59 to return the spool 58 to a closed position. When the spool 58 is fully depressed and released, a regulated amount of an enhancing agent is discharged into the basket 24. As will be understood from FIGS. 6 and 7, the amount of additive which is discharged depends upon the number of times the spool 58 is depressed.

Numerous types of enhancing agents exist in the art, including preservatives, vitamin supplements and agents for purifying water, removing odors, improving taste and destroying bacteria and microbial pathogens. The enhancing agents may be in the form of a liquid, powder or pellet and may be added to the basket 24 directly or with the dispenser 25.

Figure 8:
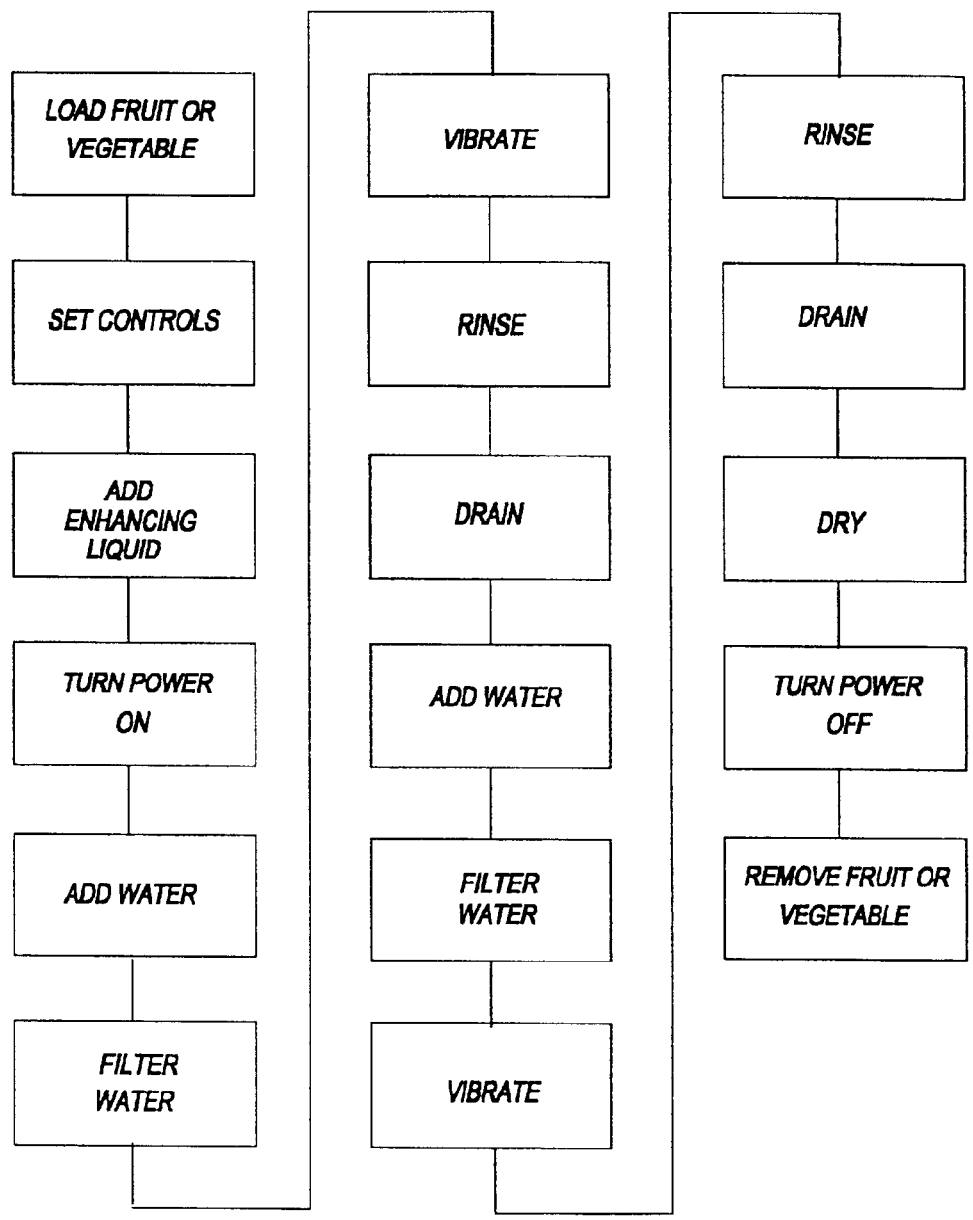
FIG. 8 is a block diagram of a method for cleaning fruits and vegetables.

A preferred manner of using the invention is disclosed in the block diagram of FIG. 8. It will be appreciated that the manner of practicing the invention can be varied somewhat from the block diagram. By way of example, the sonic generator 27 may be a single or dual frequency sonic generator. Further, important benefits can be derived without the dispenser, filter and/or dryer. Still further, an enhancing additive can be added before or after the controls are set.

Figure 4:
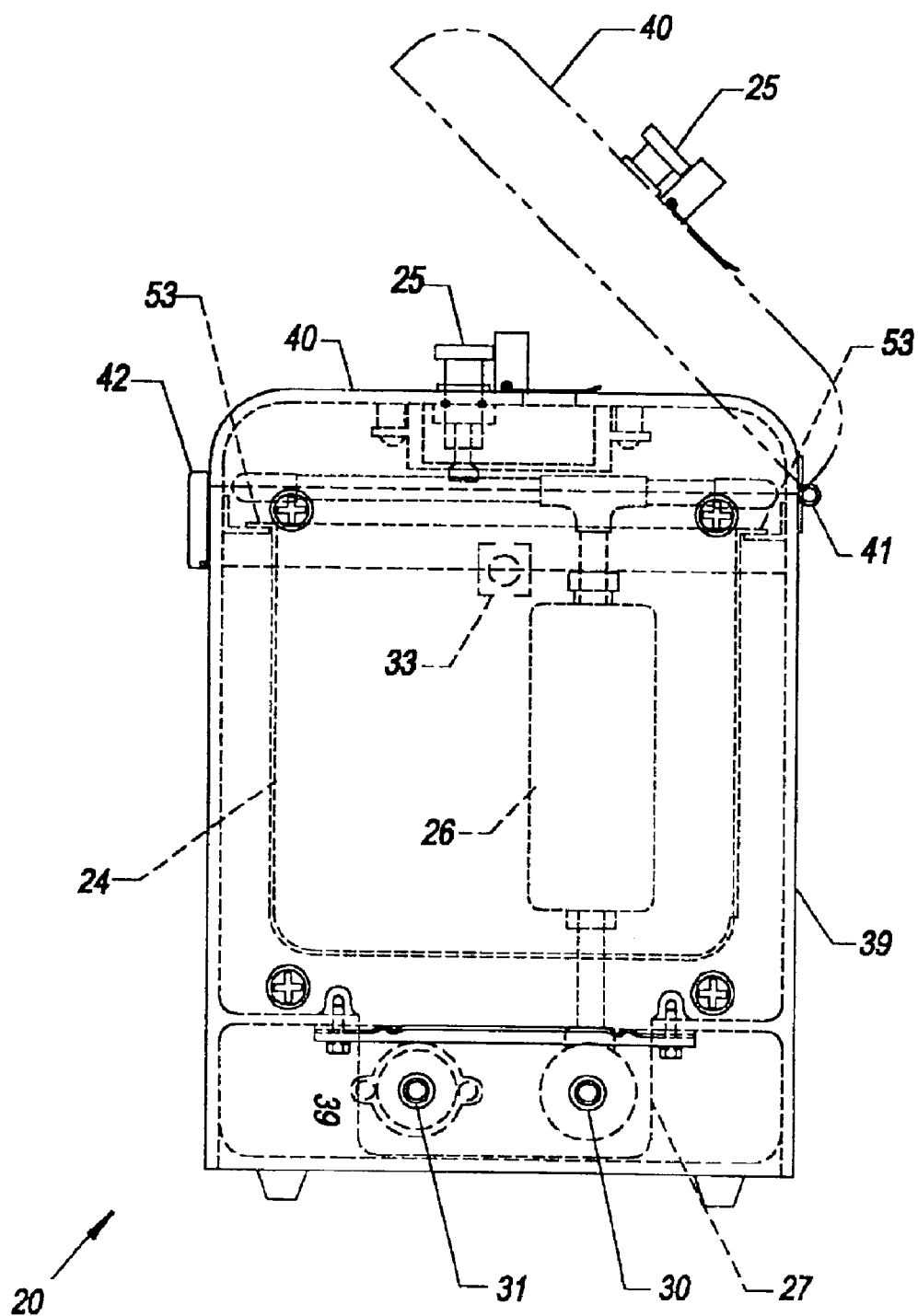
FIG. 4 is a left end view of the fruit and vegetable washer.
Figure 5:
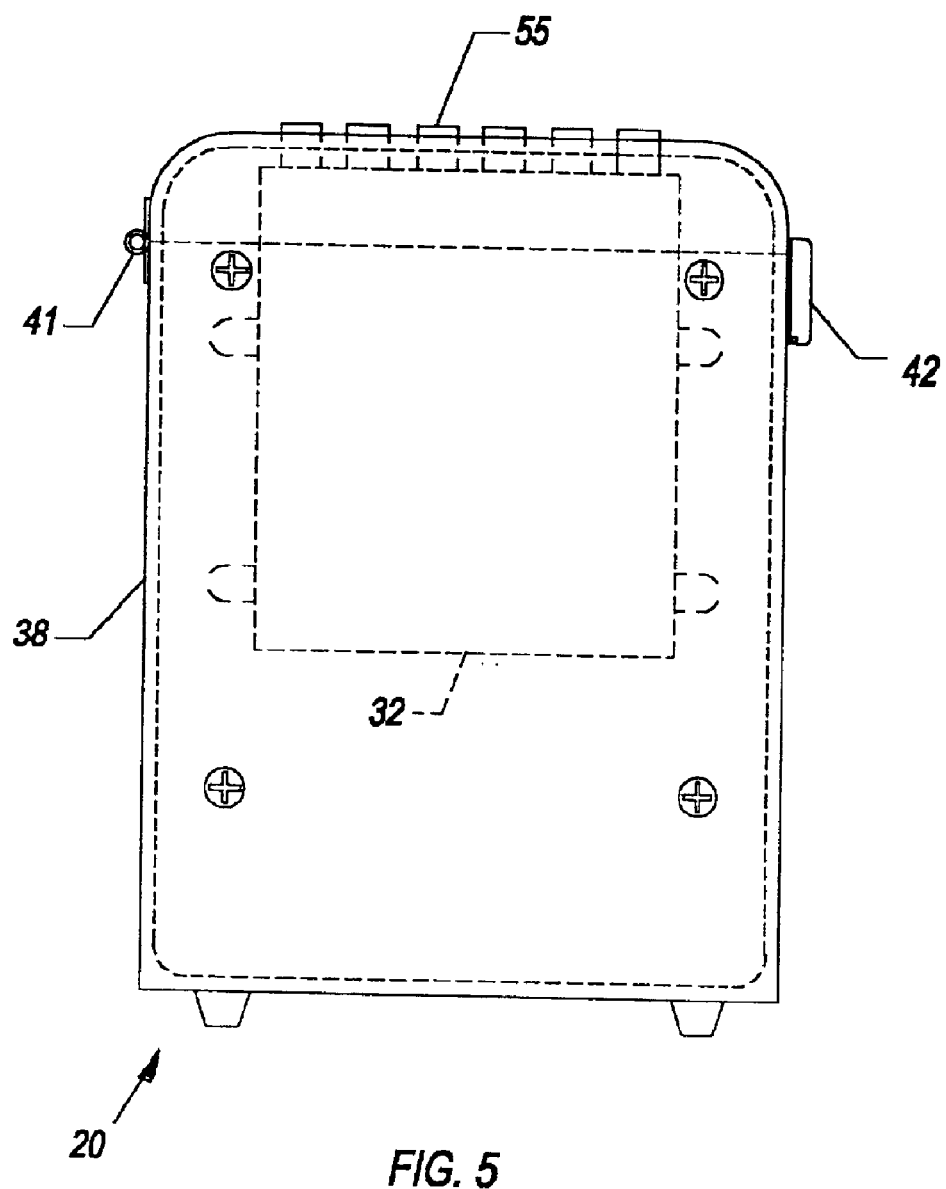
FIG. 5 is a right end view of the fruit and vegetable washer.

Returning now to FIG. 8, the first step in the method is to open the top cover 40 as shown in FIG. 4 and load the basket 24 with a fruit or vegetable. After loading the basket 24, push buttons 55 are selected and depressed and an enhancing substance, if desired, is added by depressing the spool valve 58, one or more times. The power is actuated, causing a sequence of steps to automatically occur. The first step is the opening of the inlet valve 30 to allow water from the faucet 48 to pass through the filter 26, through the spray head 28, into the tank 37.

The optional heating element 36, if desired, may be utilized to increase the effectiveness of the cleaning and disinfecting process. When the water level reaches the level switch 33, the inlet valve 30 closes and the sonic generator 27 is actuated. After the liquid in the tank 37 has been agitated by the sonic generator 27 for a pre-set time, the inlet 30 and outlet 31 valves open to begin a preset rinse cycle. During the rinse cycle, water enters the tank 37 through the inlet valve 30, filter 26 and spray head 28 and drains through the outlet valve 31 and outlet tube 35 into the sink 22. During the rinse cycle, the sonic generator 27 preferably operates to contribute to increase the effectiveness of the rinse cycle.

The rinse cycle is terminated by closing the outlet valve 31. The sonic generator 27 may or may not continue to operate. When the water level in the tank 37 reaches the water level switch 33, the inlet valve closes 30 and the sonic generator 27, if idle, is reactivated, followed by a second rinse cycle. At the end of the rinse cycle, the tank 37 is fully drained of water. The exhaust fan 29 and heating element 36 may then be activated to dry the fruit or vegetable. Power is terminated to end the process. The top cover 40 is opened and the fruit or vegetable is removed.

From the above, it will be apparent that this invention solves current problems and provides numerous benefits heretofore unavailable. Harmful contaminates are removed from fruits and vegetables and enhancing substances improve flavor, add nutrition and/or improve the cleaning and disinfecting process.

Although only a single embodiment of our invention has been disclosed, it will be appreciated that other embodiments can be derived by persons skilled in the art by changes, such as substitutions of parts, elimination of parts and inversions of parts, as well as changes in configuration and arrangement of parts.

We claim:

1. A household appliance to clean and disinfect fruits and vegetables comprising: a tank; a removable basket mounted in the interior of said tank for holding said fruits and vegetables; a sonic generator below said basket in the interior of said tank for agitating water in said tank; a spray head above said basket for distributing and spraying said water on to said fruits and vegetables in said tank: a means for automatically admitting household water into said tank; a means for automatically controlling the amount of said water in said tank; a means for automatically draining said household water from said tank; controls for operating said household appliance for various types of fruits and vegetables; a means for draining said household water from said tank: and a means for drying said fruits and vegetable in said tank, said means comprising openings and an exhaust fan for flowing air through said tank.

2. The household appliance recited in claim 1 further comprising a means in said appliance for filtering said household water before said water is admitted into said tank.

3. The household appliance recited in claim 1 further comprising a means for heating said household water in said tank.

4. The household appliance recited in claim 1 wherein said sonic generator is a dual frequency sonic generator.

5. The household appliance recited in claim 1 further comprising an enhancing agent.

6. The household appliance recited in claim 5 wherein said enhancing agent is a flavor enhancing agent.

7. The household appliance recited in claim 5 wherein said enhancing agent is a preservative.

8. The household appliance recited in claim 5 wherein said enhancing agent is a bactericidal cleaning agent.

9. The household appliance recited in claim 5 wherein said enhancing agent is a nutritional enhancing agent.

10. The household appliance recited in claim 5 wherein said enhancing agent is a liquid.

11. The household appliance recited in claim 10 further comprising a dispenser for discharging said liquid enhancing agent into said tank.

12. The household appliance recited in claim 5 wherein said enhancing agent is a powder.

13. The household appliance recited in claim 5 wherein said enhancing agent is a pellet.

14. A household appliance for cleaning and disinfecting fruits and vegetables comprising: a housing, said housing including a basket for holding said fruits and vegetables, a liquid or powder dispenser mounted in said housing, a filter mounted in said housing for filtering water admitted into said housing, a sonic generator mounted in said housing for agitating said water in said housing, a spray head mounted in said housing for distributing and spraying said water on said fruits and vegetables, an exhaust fan mounted in said housing for exhausting air from said housing, a pair of solenoid water valves admitting and draining said water from said housing, a control unit mounted in said housing for controlling an operation of said appliance, a water level switch mounted in said housing for limiting the amount of water in said housing, a pair of hoses mounted in said housing for connecting said housing to a household water source and for draining said water from said housing; a heating element mounted in said tank for heating said water in said tank, a cover pivotally mounted to said tank, and a control unit mounted in said tank for operating said appliance.

15. The household appliance recited in claim 14 further comprising a liquid dispenser mounted to said housing for discharging an enhancing fluid into said housing.

16. The household appliance recited in claim 14 wherein said sonic generator is an audio frequency sonic generator.

17. The household appliance recited in claim 14 wherein said sonic generator is an ultrasonic frequency sonic generator.

18. The household appliance recited in claim 14 wherein said sonic generator is a dual frequency sonic generator comprising an audio frequency generator and an ultrasonic frequency generator.

19. The household appliance recited in claim 14 further comprising a pair of detachable covers mounted to opposite sides of said tank for covering said control section and said valve and filter section of said housing.

20. The household appliance recited in claim 14 further comprising a fan for drying said fruit or vegetable.

21. The household appliance recited in claim 14 further comprising a fan for drying said fruit or vegetable.

22. A method for cleaning and disinfecting fruits or vegetables comprising the steps of connecting a cleaning and disinfecting appliance to a household water system; loading a tank of said appliance with a fruit or a vegetable; setting controls of said appliance for automatically controlling a series of events in said appliance, comprising admitting said water from said household water system into said tank; agitating said water with a sonic generator of said appliance; spraying water on to said fruit or vegetable from a spray head above said fruit or vegetable, draining said water from said appliance; drying said fruit or vegetable by flowing outside air through said tank and exhausting said outside air from said tank with a fan and removing said fruit or vegetable from said appliance.

23. The method for cleaning and disinfecting fruits or vegetables recited in claim 22 further comprising the step of adding an enhancing agent to said tank prior to said series of automatic events.

24. The method for cleaning and disinfecting fruits or vegetables recited in claim 22 wherein said automatic series of events includes the heating of said household water.

25. The method for cleaning and disinfecting fruits or vegetables recited in claim 22 wherein said automatic series of events further comprises a second admission of water from said household water system into said tank; a second agitation of said water by said sonic generator of said appliance; and a second draining of said water from said appliance.

26. The method for cleaning and disinfecting fruits or vegetables recited in claim 22 wherein said series of events further comprises filtering said household water when said water is admitted into said tank.

27. The method for cleaning and disinfecting fruits or vegetables recited in claim 22 wherein said automatic series of events further comprises rinsing said fruit and vegetables in said tank.

* * * * *